United States Patent [19]
Tamura

[11] Patent Number: 5,736,385
[45] Date of Patent: Apr. 7, 1998

[54] METHOD FOR PRODUCING OPTICALLY ACTIVE α-HYDROXY ACID OR α-HYDROXYAMIDE USING A CYANO ION DETECTOR AND SUBSTRATE CONCENTRATION REGULATOR

[75] Inventor: Koji Tamura, Yokohama, Japan

[73] Assignee: Nitto Chemical Industry Co., Ltd., Tokyo, Japan

[21] Appl. No.: 556,085

[22] Filed: Nov. 9, 1995

[30] Foreign Application Priority Data

Nov. 11, 1994 [JP] Japan ............... 6-299109

[51] Int. Cl.$^6$ ............... C12P 41/00; C12P 13/02; C12P 11/00; C12P 7/40
[52] U.S. Cl. ............... 435/280; 435/129; 435/130; 435/136; 435/146; 422/82.03
[58] Field of Search ............... 435/280, 129, 435/130, 136, 146; 422/82.03

[56] References Cited

U.S. PATENT DOCUMENTS

| | | | |
|---|---|---|---|
| 4,351,743 | 9/1982 | Hashimoto | 252/408 |
| 5,283,193 | 2/1994 | Yamamoto et al. | 435/280 |
| 5,326,702 | 7/1994 | Endo et al. | 435/129 |

FOREIGN PATENT DOCUMENTS

| | | |
|---|---|---|
| 0 486 289 | 5/1992 | European Pat. Off. . |
| 0 527 553 | 2/1993 | European Pat. Off. . |

OTHER PUBLICATIONS

Process Biochemistry, 1980, pp. 18–23, D.B. Kell E.A., 'The Role of Ion–Selective Electrodes in Improving Fermentation Yields'.

*Primary Examiner*—Sandra E. Saucier
*Attorney, Agent, or Firm*—Sughrue, Mion, Zinn, Macpeak & Seas, PLLC

[57] ABSTRACT

A reaction system, wherein a cyanohydrin is converted into an optically active α-hydroxy acid or α-hydroxyamide via a treatment with a microorganism, is provided with an automatic cyanohydrin controller comprising a cyano ion detector, a regulator and a cyanohydrin supplier linked thereto. The reaction is performed while automatically controlling the cyanohydrin concentration.

Thus cyanohydrin can be supplied under automatic control at a relatively low and constant concentration on the basis of its consumption ratio. The reaction rate of the catalyst can be continuously regarded as the rate-limiting factor. As a result, a decrease in the enzymatic activity during the reaction can be suppressed and an optically active α-hydroxy acid or α-hydroxyamide can be efficiently obtained at a high yield.

12 Claims, 1 Drawing Sheet

METHOD FOR PRODUCING OPTICALLY ACTIVE α-HYDROXY ACID OR α-HYDROXYAMIDE USING A CYANO ION DETECTOR AND SUBSTRATE CONCENTRATION REGULATOR

FIELD OF THE INVENTION

This invention relates to a method for producing an optically active α-hydroxy acid or α-hydroxyamide from a cyanohydrin via treatment with a microorganism. More particularly, it relates to a method for producing an optically active α-hydroxy acid or α-hydroxyamide by maintaining the cyanohydrin concentration at a definite level with the use of an automatic cyanohydrin controller.

Optically active α-hydroxy acids or α-hydroxyamides are highly important compounds used for synthesizing drugs and agricultural chemicals.

BACKGROUND OF THE INVENTION

Nitrilase is an enzyme capable of hydrolyzing a nitrile into the corresponding acid, and nitrile hydratase is an enzyme capable of hydrating a nitrile into the corresponding amide. Some methods have been reported for producing optically active α-hydroxy acids or α-hydroxyamides from cyanohydrins with the use of microorganisms expressing these enzyme activities [see, for example, JP-A-2-84198 (corresponding to U.S. Pat. No. 5,283,193), JP-A-3-277292, EP-A-0 449 648 (corresponding to JP-A-4-99495, JP-A-4-99496 and JP-A-4-218385, respectively), JP-A-4-222591, JP-A-5-95795 (corresponding to U.S. Pat. No. 5,296,373), JP-A-5-192189 (corresponding to U.S. Pat. No. 5,326,702), JP-A-5-244968 and JP-A-6-237789 (corresponding to EP-A-0 610 048); the term "JP-A" as used herein means an "unexamined published Japanese patent application"; and Appl. Env. Microbiol., 57 3028 (1991)].

In general, reaction catalysts such as microbial cells or enzymes such as nitrilase and nitrile hydratase are highly sensitive to cyanohydrins, and aldehydes and prussic acid constituting the same. In the methods cited above, a conversion reaction is carried out by treating a relatively low concentration cyanohydrin solution with microbial cells or an enzyme. Thus, it is difficult to obtain the product at a high concentration by these methods.

In order to obtain a high concentration product, it is necessary to repeatedly add cyanohydrin to the reaction system. Thus, it is necessary to perform the complicated operation of supplying the cyanohydrin while also measuring the cyanohydrin concentration to make up for the loss thereof. This causes problems in industrial application.

SUMMARY OF THE INVENTION

The present inventors have discovered that a cyanohydrin may attain dissociation equilibrium into an aldehyde and prussic acid in an aqueous medium at a definite equilibrium constant depending upon the pH. This dissociation equilibrium may also be established under optimum reaction conditions (e.g., pH, temperature, ionic strength) of microbial cells or an enzyme. That is, the prussic acid concentration is always directly proportional to the cyanohydrin concentration. The present inventors have further discovered that the ion selective electrode methods (JIS K 0109-1974 and JIS K 0102-1985) with a cyano ion electrode may be used as a means for determining the presence and amount of cyano ion originating in prussic acid. Based on these findings, the present inventors have also discovered that the cyanohydrin concentration in a reaction system can be automatically controlled at an arbitrary level by continuously monitoring the cyano ion concentration in the reaction system with a cyano ion detector and linking a cyanohydrin supplier with this cyano ion detector and a regulator.

Accordingly, the present invention provides a method for producing an optically active α-hydroxy acid or α-hydroxyamide comprising treating a cyanohydrin represented by formula (I) with a microorganism, which may have been treated, having a nitrilase or nitrile hydratase activity to convert said cyanohydrin into an optically active α-hydroxy acid or α-hydroxyamide represented by formula (II), wherein an automatic cyanohydrin controller comprising a cyano ion detector, a regulator and a cyanohydrin supplier linked thereto is furnished to perform the reaction while automatically controlling the cyanohydrin concentration.

The above-noted formula (I) and formula (II) are indicated as follows:

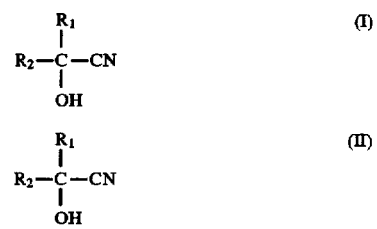

wherein $R_1$ represents a hydrogen atom or a methyl group; $R_2$ represents a substituted or unsubstituted alkyl group (provided that $R_2$ is not a methyl group when $R_1$ is a methyl group), a substituted or unsubstituted alkenyl group, a substituted or unsubstituted aryl group, a substituted or unsubstituted aralkyl group, a substituted or unsubstituted cycloalkyl group, a substituted or unsubstituted alkoxy group, a substituted or unsubstituted aryloxy group, or a substituted or unsubstituted, saturated or unsaturated heterocyclic group; and X represents a carboxyl group or an amide group.

When the cyanohydrin in the reaction system is replaced by an aldehyde and prussic acid, these substances quickly come to equilibrium with the cyanohydrin. Thus, the object of the present invention is achieved.

Moreover, the present inventors have discovered a method for relieving the toxicity of an aldehyde on microbial cells or enzymes by adding sulfite ion in the presence of a cyanohydrin or an aldehyde and prussic acid to thereby form an aldehyde-sulfurous acid complex (see, JP-A-5-192189 cited above). In this case, an equilibrium is quickly reached among and between cyanohydrin/aldehyde/prussic acid/aldehyde-sulfurous acid complex/sulfite ion, and thus the object of the present invention is attained.

DETAILED DESCRIPTION OF THE INVENTION

Figure 1:
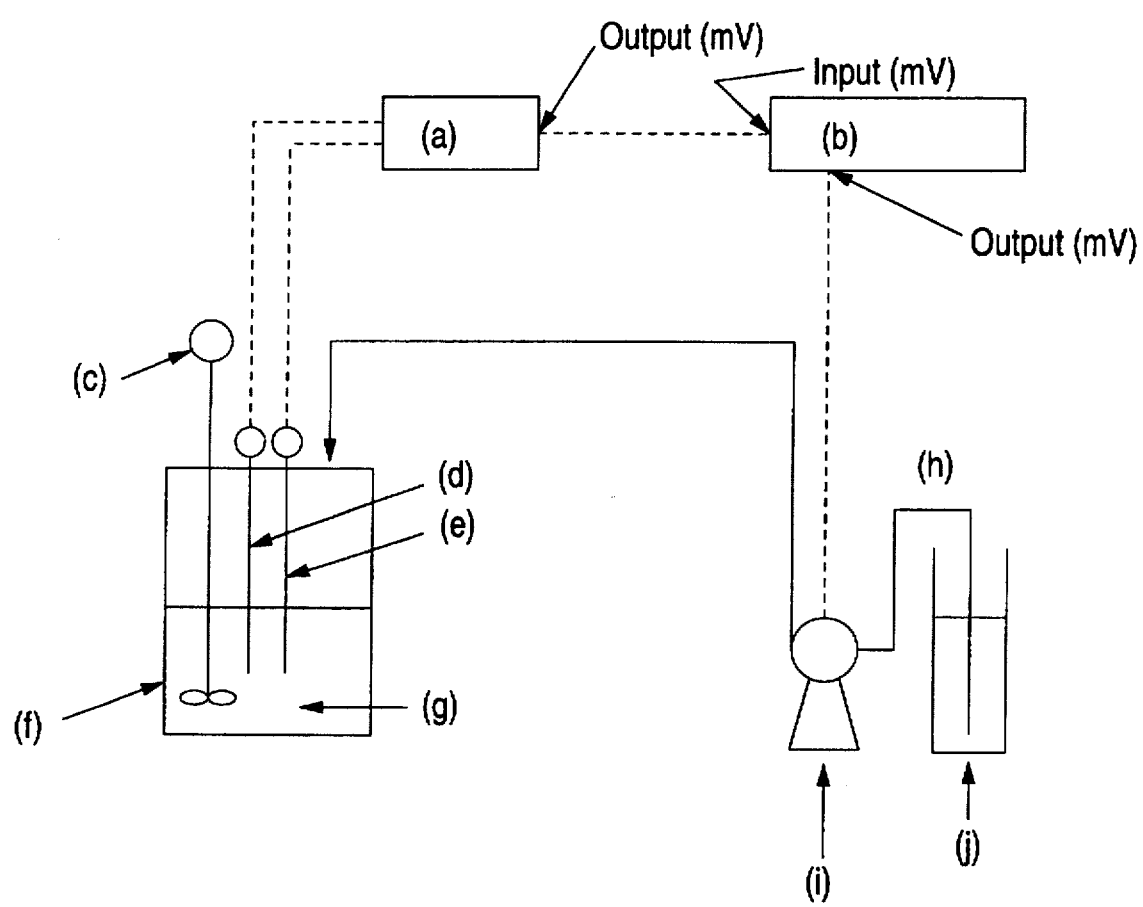
FIG. 1 is a diagram which shows the constitution of an automatic cyanohydrin controller.

As FIG. 1 shows, the automatic cyanohydrin controller of the present invention comprises a cyano ion detector (a) having a cyano ion electrode (e) and a reference electrode (d) as a detection unit, and a regulator (b) and a cyanohydrin supplier (h) (consisting of cyanohydrin-supplying pump/valve (i) and cyanohydrin pool tank (j)) linked thereto. The cyanohydrin concentration in the reaction system is continuously monitored with the cyano ion detector (a). The data thus obtained are sent as voltage signals to a regulator (b) having a built-in amplifier, ON/OFF relay, etc. and the cyanohydrin supplier (h) linked thereto. Thus, the cyanohydrin concentration can be controlled at an arbitrary level. For example, a cyano ion electrode (e) and a reference electrode (d) as described in JIS K 0109-1974 and JIS K 0102-1985 may be used as the cyano ion detecting unit.

The cyano ion concentration in the reaction system is set within the detectable range of the cyano ion detector (a), i.e., 0.01 to 10 mM, and preferably 0.1 to 5 mM. By controlling the cyanohydrin concentration in such a manner as to regulate the cyano ion concentration within this range, the enzymatic inhibition by the microbial cells, etc. can be suppressed and the desired product can be accumulated at a high concentration.

The microorganisms to be used in the present invention are not particularly restricted, so long as they have a nitrilase or nitrile hydratase activity.

Examples of microorganisms having a nitrilase activity include those belonging to the genera Pseudomonas, Alcaligenes, Acinetobacter, Caseobacter, Corynebacterium, Brevibacterium, Nocardia, Rhodococcus, Gordona, Arthrobacter, Bacillus, Aureobacterium, Enterobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium and Rhodopseudomonas. As particular examples thereof, the following microorganisms can be cited; Pseudomonas sp. BC13-2 (FERM BP-3319), do. BC15-2 (FERM BP-3320), do. SK13 (FERM BP3325), do. SK31 (FERM P-11310), do. SK87 (FERM P-11311), do. BC-18 (FERM BP-4536), Pseudomonas synxanta IAM 12356, Alcaligenes sp. BC12-2 (FERM P-11263), do. BC20 (FERM P11264), do. BC35-2 (FERM BP-3318), do. BC24 (FERM P-12063), Acinetobacter sp. BC9-2 (FERM BP-3317), Caseobacter sp. BC4 (FERM BP-3316), do. BC23 (FERM P-11261), Corynebacterium nitrilophilus ATCC 21419, Brevibacterium acetylicum IAM 1790, Brevibacterium helvolum ATCC 11822, Nocardia sp. N-775 (FERM P-4447), Nocardia asteroides IFO 3384, Nocardia calcarea KCCA0191, Nocardia polychromogenes IFM 19, Rhodococcus sp. SK70 (FERM P-11304), do. SK92 (FERM BP-3324), do. HR11 (FERM P-11306), do. HT29-7 (FERM BP-3857), Rhodococcus rhodochrous ATCC 12674, do. ATCC 19140, do. ATCC 33258, Rhodococcus erythropolis IFM 155, do. IFO 12320, do. IFO 12538, do. IFO 12540, Gordona terrae MA-1 (FERM BP-4535), Arthrobacter sp. SK103 (FERM P-11300), do. HR1 (FERM BP-3323), do. HR4 (FERM P-11302), Arthrobacter oxydans IFO 12138, Bacillus subtilis ATCC 21697, Bacillus licheniformis IFO 12197, Bacillus megaterium ATCC 25833, Aureobacterium testaceum IAM 1561, Enterobacter sp. SK12 (FERM BP-3322), Escherichia coli IFO 3301, Micrococcus luteus ATCC 383, Micrococcus varians IAM 1099, Micrococcus roseus IFO 3768, Streptomyces griseus IFO 3355, Flavobacterium sp. SK150 (FERM P-11645), Flavobacterium flavescens ATCC 8315, Aeromonas punctata IFO 13288, Mycoplana dimorpha ATCC 4297, Cellulomonas fimi IAM 12107, Erwinia herbicola IFO 12686 and Candida guilliermondii IFO 0566.

Other microorganisms capable of producing α-hydroxy acids are described in the patents cited above and are hereby incorporated by references.

On the other hand, examples of microorganisms having a nitrile hydratase activity include those belonging to the genera Rhodococcus, Corynebacterium, Pseudomonas, Arthrobacter, Alcaligenes, Bacillus, Bacteridium, Micrococcus, Brevibacterium and Nocardia. As particular examples thereof, the following microorganisms can be cited; Rhodococcus sp. HT40-6 (FERM P-11774), Rhodococcus rhodochrous ATCC 33278, Rhodococcus erythropolis IFO 12320, Corynebacterium nitrilophilus ATCC 21419, Pseudomonas sp. SK87 (FERM P-11311), Arthrobacter sp. HR1 (FERM BP-3323), Alkaligenes sp. BC16-2 (FERM BP-3321), Brevibacterium acetylicum IAM 1790, Nocardia erythropolis IFO 12539 and do. IFO 12540.

Other microorganisms capable of producing α-hydroxyamides are described in the patents cited above and are hereby incorporated by reference.

Among these microorganisms, Pseudomonas sp. BC13-2, do. BC15-2, do. SK13, do. SK31, do. SK87 and do. BC-18, Alcaligenes sp. BC12-2, do. BC20, do. BC35-2, do. BC16-2 and do. BC24, Acinetobacter sp. BC9-2, Caseobacter sp. BC4 and do. BC23, Nocardia sp. N-775, Rhodococcus sp SK70, do. SK92, do. HR11, do. HT40-6 and do. HT29-7, Gordona terrae MA-1, Arthrobacter sp. SK103, do. HR1 and do. HR4, Enterobacter sp. SK12 and Flavobacterium sp. SK150 were isolated from nature by the present applicant and described respectively in JP-A-5-192189 (corresponding to U.S. Pat. No. 5,326,702), JP-A-4-218385 (corresponding to EP-A-0 449 648), JP-A-6-237789 (corresponding to EP-A-0 610 048), each cited above, and JP-A-6-284899 (corresponding to EP-A-0 610 049). Each of these strains has been deposited at the National Institute of Bioscience and Human-Technology, Agency of Industrial Science and Technology, Tsukuba, Japan under the accession number provided above.

Other microorganisms can be easily obtained from the American Type Culture Collection, USA (ATCC), Institute of Applied Microbiology, the University of Tokyo, Tokyo, Japan (IAM), Kaken Pharmaceutical Co., Ltd., Japan (KCC), Institute for Fermentation, Osaka, Japan (IFO) and the Institute for Chemobiodynamics, the Chiba University, Chiba, Japan (IFM).

In the cyanohydrins of formula (I), $R_1$ is a hydrogen atom or a methyl group; $R_2$ is a substituted or unsubstituted alkyl group (provided that $R_2$ is not a methyl group when $R_1$ is a methyl group), a substituted or unsubstituted alkenyl group, a substituted or unsubstituted aryl group, a substituted or unsubstituted aralkyl group, a substituted or unsubstituted cycloalkyl group, a substituted or unsubstituted alkoxy group, a substituted or unsubstituted aryloxy group, or a substituted or unsubstituted, saturated or unsaturated heterocyclic group. Typical examples thereof are compounds wherein the alkyl, alkenyl, aralkyl, cycloalkyl and alkoxy groups have respectively 1 to 6, 2 to 5, 7 to 9, 3 to 6 and 1 to 5 carbon atoms.

Examples of the substituents include alkyl, alkoxy, aryl, aryloxy and acyl groups, halogen atoms such as chlorine or bromine, and hydroxyl, amino, nitro and thiol groups. The heterocyclic group may be exemplified by those having at least one heteroatom selected from among nitrogen, oxygen and sulfur.

Particular examples thereof include lactonitrile, 3-chlorolactonitrile, 2-hydroxy-n-propionitrile, 2-hydroxy-n-butyronitrile, 2-hydroxy-isobutyronitrile, 4-methylthio-2-hydroxybutyronitrile, isobutylaldehyde cyanohydrin, 2-hydroxy-n-hexylonitrile, 2,4-dihydroxy-3,3-dimethylbutyronitrile, 2-hydroxy-n-heptylonitrile, 2-hydroxy-n-octylonitrile, acrolein cyanohydrin, methacrylaldehyde cyanohydrin, 1-butene-4-carboxyaldehyde cyanohydrin, 1-pentene-5-carboxyaldehyde cyanohydrin, mandelonitrile, 2-chloromandelonitrile, 3-chloromandelonitrile, 4-chloromandelonitrile, 4-bromomandelonitrile, 4-methylmandelonitrile, 4-isopropylmandelonitrile, 4-methoxymandelonitrile, 4-phenylmandelonitrile, 4-phenoxymandelonitrile, 3-phenoxymandelonitrile, 4-hydroxymandelonitrile, 4-nitromandelonitrile, 4-aminomandelonitrile, 4-methylthiomandelonitrile, 2-naphthylaldehyde cyanohydrin, 3-phenyllactonitrile, 3-phenylpropionealdehyde cyanohydrin, 4-phenylbutylaldehyde cyanohydrin, cyclopropylaldehyde cyanohydrin, cyclobutylaldehyde cyanohydrin, cyclopentylaldehyde cyanohydrin, cyclohexylaldehyde cyanohydrin, methoxyaldehyde cyanohydrin, n-pentoxyaldehyde cyanohydrin, phenoxyaldehyde cyanohydrin, 2-thiophenecarboxyaldehyde cyanohydrin, 2-pyrrolecarboxyaldehyde cyanohydrin, 2-furaldehyde cyanohydrin, 2-pyridinecarboxyaldehyde cyanohydrin and 2-hydroxy-2-phenylpropionitrile.

The invention may be practiced according to the following description. However, many variations are possible within the scope of the described embodiments.

A cyanohydrin is hydrated or hydrolyzed by contacting the cyanohydrin or the aldehyde and prussic acid constituting the same with a microorganism, which has been optionally treated (disrupted cells, crude or purified enzyme, immobilized cells or enzyme, etc.), in an aqueous medium.

Desalted water, aqueous solutions of salts such as sodium sulfate, sodium acetate, sodium chloride, potassium chloride, sodium phosphate or ammonium chloride, neutral or alkaline phosphate buffer solutions and borate buffer solutions may be used as the aqueous medium. The concentration thereof ranges from 1 mM to the saturation concentration, preferably from 10 to 100 mM. The concentration of the cells, which may have been treated, is from 0.01 to 5.0% by weight in terms of dry matter. The reaction temperature may be adjusted to a level giving a high productivity within a range of from 0° to 50° C., preferably from 10° to 35° C.

In the present invention, the cyanohydrin concentration is set to such a level as to provide a cyano ion concentration within the detectable range of the cyano ion detector (i.e., from 0.01 to 10 mM, preferably from 0.1 to 5 mM).

The appropriate concentration may be attained by preliminarily forming a calibration curve, showing a correlation between the cyano ion concentration (mV) indicated by the cyan ion detector and the mandelonitrile concentration (mM), and then regulating the cyano ion concentration indicated by the cyan ion detector within a definite range.

When the cyanohydrin or the aldehyde and prussic acid show low solubilities, an organic solvent or a surfactant may be added at such a level as not to effect the reaction to thereby elevate the solubilities.

The concentration of sulfite ion, if added, is not particularly limited but can be determined depending on the kinds and concentrations of cyanohydrin and aldehyde. Usually, it ranges from 1 to 300 mM.

The optically active α-hydroxy acid or α-hydroxyamide formed in the reaction mixture can be isolated by removing the cells by, for example, centrifugation followed by treatments known to those of skill in the art such as concentration, electrodialysis, ion exchange, extraction, crystallization, etc.

To further illustrate the present invention in greater detail, and not by way of limitation, the following Examples will be given.

EXAMPLE 1

As FIG. 1 shows, a reaction system was provided with an automatic cyanohydrin controller (h), and R-mandelic acid was produced by hydrolyzing mandelonitrile using Gordona terrae MA-1.

In this apparatus, the power supply of the feedstock cyanohydrin supplier (h) was switched using a regulator which consisted of an amplifier, an ON/OFF relay, etc. The regulator was used to regulate the output voltage from the cyano ion detector (a) within a definite range depending upon the cyano ion concentration in the reaction mixture (g). Thus, in a reaction tank (f) equipped with a stirrer (c), the concentration of the feedstock cyanohydrin in the reaction mixture was controlled within a definite range.

The hydrolysis was performed in a 50 mM phosphate buffer solution in the presence of 100 mM of sodium sulfite with a cell concentration ($OD_{630}$) of 4.2, at a pH of 8.2 to 8.4, at 30° C. for 22 hours.

The concentration of the feedstock cyanohydrin was automatically controlled by preliminarily forming a calibration curve and then regulating the cyano ion concentration indicated by the detector within a definite range. The calibration curve showed a correlation between the cyano ion concentration (mV) indicated by the cyan ion detector and the mandelonitrile concentration (mM).

Table 1 shows the results.

TABLE 1

| Regulation range of mandelonitrile 17.3–19.5 mM | |
|---|---|
| Conc. of R-mandelic acid formed | 1315 mM |
| Optical purity of R-mandelic acid | 98.9% ee |
| Conc. of unreacted mandelonitrile | 18.0 mM |
| Conversion ratio | 98.6% |

EXAMPLE 2

In accordance with the method of Example 1, mandelonitrile was hydrated using Rhodococcus sp. HT40-6 instead of Gordona terrae MA-1 to thereby produce S-mandelamide.

The hydration was performed in a 50 mM phosphate buffer solution in the presence of 100 mM of sodium sulfite with a cell concentration ($OD_{630}$) of 10.0, at a pH of 8.2 to 8.4, at 30° C. for 22 hours.

Table 2 shows the results.

TABLE 2

| Regulation range of mandelonitrile 17.0–20.0 mM | |
|---|---|
| Conc. of S-mandelamide formed | 1522 mM |
| Optical purity of S-mandelamide | 95.0% ee |
| Conc. of unreacted mandelonitrile | 19.5 mM |
| Conversion ratio | 98.7% |

EXAMPLE 3

In accordance with the method of Example 1, 3-chloromandelonitrile was hydrolyzed to thereby produce R-3-chloromandelic acid.

The hydrolysis was performed in a 50 mM phosphate buffer solution in the presence of 100 mM of sodium sulfite with a cell concentration ($OD_{630}$) of 4.2, at a pH of 8.6 to 8.8, at 15° C. for 22 hours.

Table 3 shows the results.

TABLE 3

| Regulation range of 3-chloromandelonitrile 8.4–9.5 mM | |
| --- | --- |
| Conc. of R-3-chloromandelic acid formed | 804 mM |
| Optical purity of R-3-chloromandelic acid | 99.0% ee |
| Conc. of unreacted 3-chloromandelonitrile | 8.4 mM |
| Conversion ratio | 99.0% |

EXAMPLE 4

In accordance with the method of Example 1, 3-phenyllactonitrile was hydrolyzed to thereby produce S-3-phenyllactic acid.

The hydrolysis was performed in a 50 mM phosphate buffer solution in the presence of 100 mM of sodium sulfite with a cell concentration ($OD_{630}$) of 18.5, at a pH of 8.4 to 8.6, at 30° C. for 168 hours.

Table 4 shows the results.

TABLE 4

| Regulation range of phenyllactonitrile 8.0–10.0 mM | |
| --- | --- |
| Conc. of S-phenyllactic acid formed | 140 mM |
| Optical purity of S-phenyllactic acid | 77.1% ee |
| Conc. of unreacted phenyllactonitrile | 8.5 mM |
| Conversion ratio | 94.3% |

EXAMPLE 5

In accordance with the method of Example 1, 2-hydroxy-4-phenylbutyronitrile (hereinafter referred to as HPBN) was hydrolyzed to thereby produce S-2-hydroxy-4-phenylbutyric acid (hereinafter referred to as S-HPBA).

The hydrolysis was performed in a 50 mM phosphate buffer solution in the presence of 100 mM of sodium sulfite with a cell concentration ($OD_{630}$) of 53.7, at a pH of 8.5 to 8.6, at 20° C. for 48 hours.

Table 5 shows the results.

TABLE 5

| Regulation range of HPBN 5.0–15.0 mM | |
| --- | --- |
| Conc. of S-HPBA formed | 399 mM |
| Optical purity of HPBA | 99.0% ee |
| Conc. of unreacted HPBN | 5.2 mM |
| Conversion ratio | 98.7% |

EXAMPLE 6

The procedure of Example 1 was repeated but the mandelonitrile was substituted with sodium cyanide and benzaldehyde to thereby produce R-mandelic acid.

The reaction was performed in a 50 mM phosphate buffer solution in the presence of 100 mM of sodium sulfite with a cell concentration ($OD_{630}$) of 8.8, at a pH of 8.2 to 8.4, at 30° C. for 23 hours.

As the sodium cyanide and benzaldehyde, 47% aqueous solution of sodium cyanide (9.6 mmol/ml) and 97% benzaldehyde (9.6 mmol/ml) were used respectively. In this case, the calibration curve formed in Example 1 was used. It showed a correlation between the cyano ion concentration (mV) indicated by the cyan ion detector and the feedstock concentration (mM).

Table 6 shows the results.

TABLE 6

| Regulation range of mandelonitrile 18.0–20.0 mM | |
| --- | --- |
| Conc. of R-mandelic acid formed | 986 mM |
| Optical purity of R-mandelic acid | 98.6% ee |
| Conc. of unreacted mandelonitrile | 18.4 mM |
| Conversion ratio | 98.2% |

COMPARATIVE EXAMPLE 1

R-Mandelic acid was produced by hydrolyzing mandelonitrile using Gordona terrae MA-1 while not using a cyano ion detector (a) but while regulating the flow rate of a pump for supplying the feedstock at a constant level.

The hydrolysis was performed in a 50 mM phosphate buffer solution in the presence of 100 mM of sodium sulfite with a cell concentration ($OD_{630}$) of 4.2, at a pH of 8.2 to 8.4, at 30° C. for 22 hours.

Table 7 shows the results.

TABLE 7

| Supply rate of mandelonitrile 60.6 mmol/hr | |
| --- | --- |
| Amount of reacted mixture | 1,000 ml |
| Conc. of R-mandelic acid formed | 250 mM |
| Optical purity of R-mandelic acid | 98.5% ee |
| Conc. of unreacted mandelonitrile | 1082 mM |
| Conversion ratio | 18.8% |

COMPARATIVE EXAMPLE 2

R-Mandelic acid was produced by hydrolyzing mandelonitrile while not using a cyano ion detector (a) but while regulating the flow rate of a pump for supplying the feedstock to ¼ (constant) of that of Comparative Example 1.

The hydrolysis was performed in a 50 mM phosphate buffer solution in the presence of 100 mM of sodium sulfite with a cell concentration ($OD_{630}$) of 4.2, at a pH of 8.2 to 8.4, at 30° C. for 88 hours.

Table 8 shows the results.

TABLE 8

| Supply rate of mandelonitrile 15.2 mmol/hr | |
| --- | --- |
| Amount of reacted mixture | 1,000 ml |
| Conc. of R-mandelic acid formed | 1210 mM |
| Optical purity of R-mandelic acid | 97.0% ee |
| Conc. of unreacted mandelonitrile | 128 mM |
| Conversion ratio | 90.4% |

According to the present invention, the feedstock cyanohydrin can be supplied at a relatively low and constant concentration on the basis of the consumption ratio of the same. Thus, the reaction rate of the catalyst can be continuously regarded as the rate-limiting factor. As a result, a decrease in the enzymatic activity during the reaction can be suppressed and an optically active α-hydroxy acid or α-hydroxyamide can be efficiently obtained at a high yield.

While the invention has been described in detail and with reference to specific embodiments thereof, it will be apparent to one skilled in the art that various changes and modifications can be made therein without departing from the spirit and scope thereof.

What is claimed is:

1. A method for producing an optically active α-hydroxy acid or α-hydroxyamide comprising treating a cyanohydrin represented by formula (I) with a microorganism, which may have been treated, having a nitrilase or nitrile hydratase activity to convert said cyanohydrin into an optically active α-hydroxy acid or α-hydroxyamide represented by formula (II),

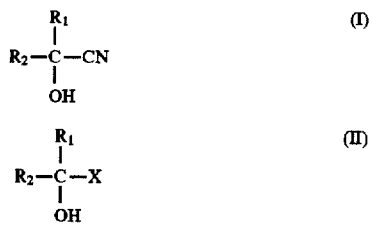

wherein $R_1$ represents a hydrogen atom or a methyl group; $R_2$ represents a substituted or unsubstituted alkyl group in which $R_2$ is not a methyl group when $R_1$ is a methyl group, a substituted or unsubstituted alkenyl group, a substituted or unsubstituted aryl group, a substituted or unsubstituted aralkyl group, a substituted or unsubstituted cycloalkyl group, a substituted or unsubstituted alkoxy group, a substituted or unsubstituted aryloxy group, or a substituted or unsubstituted, saturated or unsaturated heterocyclic group; and X represents a carboxyl group or an amide group;

wherein an automatic cyanohydrin controller comprising a cyano ion detector, a regulator and a cyanohydrin supplier linked thereto is furnished for performing the reaction while automatically controlling the cyanohydrin concentration.

2. The method for producing an optically active alpha-hydroxy acid or alpha-hydroxyamide of claim 1, wherein the cyanohydrin represented by formula (I) is formed by an aldehyde and prussic acid which equilibrate with said cyanohydrin.

3. The method for producing an optically active α-hydroxy acid or α-hydroxyamide of claim 1, wherein the reaction is performed at a cyano ion concentration of 0.01 to 10 mM.

4. The method according to claim 1, wherein the organism has not been treated.

5. The method according to claim 1, wherein the microorganism has been treated to produce disrupted cells.

6. The method according to claim 1, wherein the microorganism has been treated to produce a crude or purified enzyme.

7. The method according to claim 6, wherein the enzyme is a crude enzyme.

8. The method according to claim 6, wherein the enzyme is a purified enzyme.

9. The method according to claim 1, wherein the microorganism has been treated by immobilization to produce immobilized cells.

10. The method according to claim 1, wherein the microorganism has been treated by disrupting the microorganism to produce an immobilized enzyme.

11. The method according to claim 6, wherein the enzyme is a purified enzyme and said purified enzyme is immobilized.

12. The method according to claim 6, wherein the enzyme is a crude enzyme and the crude enzyme is immobilized.

* * * * *